United States Patent
Bruninga et al.

(10) Patent No.: US 7,027,860 B2
(45) Date of Patent: Apr. 11, 2006

(54) MICROSTIMULATOR NEURAL PROSTHESIS

(75) Inventors: Keith Walter Bruninga, Frankfort, IL (US); Lisa Wittenkeller Riedy, Naperville, IL (US); Paul Joseph Zaszczurynski, Sycamore, IL (US)

(73) Assignee: Department of Veterans Affairs, Baltimore, MD (US)

( * ) Notice: Subject to any disclaimer, the term of this patent is extended or adjusted under 35 U.S.C. 154(b) by 340 days.

(21) Appl. No.: 10/230,393

(22) Filed: Aug. 29, 2002

(65) Prior Publication Data

US 2004/0044380 A1 Mar. 4, 2004

(51) Int. Cl.
*A61N 1/00* (2006.01)

(52) U.S. Cl. .............................. 607/2; 607/40; 607/42; 607/50; 607/117

(58) Field of Classification Search ................. 607/32, 607/33, 40–49, 55–57, 60, 62, 117–118, 2; 128/903
See application file for complete search history.

(56) References Cited

U.S. PATENT DOCUMENTS

| | | | |
|---|---|---|---|
| 4,082,097 A * | 4/1978 | Mann et al. ................... 607/33 |
| 5,792,186 A * | 8/1998 | Rise .............................. 607/2 |
| 6,185,452 B1 * | 2/2001 | Schulman et al. ............. 604/20 |
| 6,415,184 B1 * | 7/2002 | Ishikawa et al. .............. 607/45 |
| 6,609,032 B1 * | 8/2003 | Woods et al. .................. 607/46 |
| 6,631,296 B1 * | 10/2003 | Parramon et al. ............. 607/61 |
| 2003/0204226 A1 * | 10/2003 | Acosta et al. ................. 607/48 |

* cited by examiner

Primary Examiner—Carl Layno
(74) Attorney, Agent, or Firm—Dykema Gossett PLLC

(57) ABSTRACT

A microstimulator or neural prosthesis is powered and operative in response to an externally applied RF signal which includes a power component and control component. A slow rise time storage circuit stores RF power during a charging period and a fast rise time triggering circuit responsive to a fast rise time input triggers the device for producing output pulses following a selected delay time. The duration of the delay controls the current level of the output pulses.

14 Claims, 3 Drawing Sheets

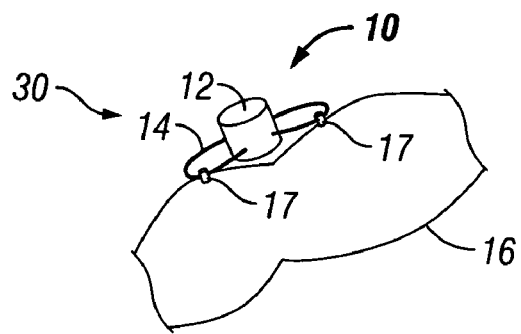
FIG. 1
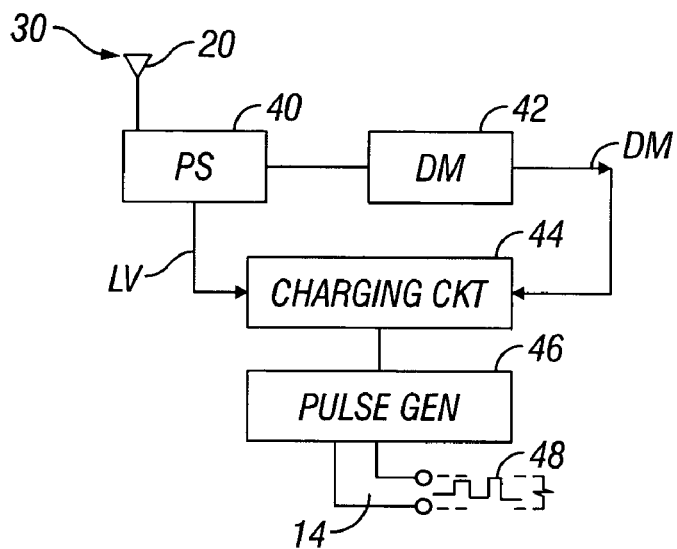
FIG. 2
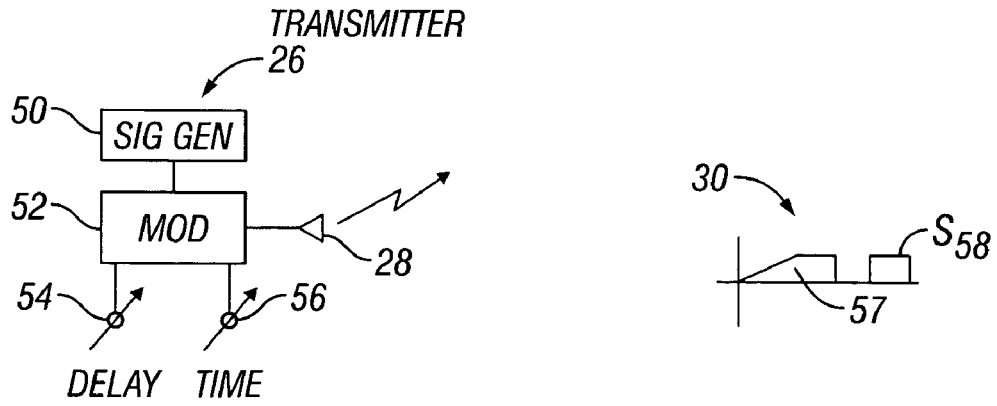
FIG. 3
FIG. 3A

MICROSTIMULATOR NEURAL PROSTHESIS

BACKGROUND OF THE INVENTION

This invention relates to an implantable microstimulator or neural prosthesis powered by an operative in response to an externally applied signal. In particular, the invention relates to a device responsive to an input signal having a power component and a control component wherein the device output is controllable in accordance with encoding associated with the input signal.

Autonomic problems occur in areas of the bowel, bladder and respiratory systems following spinal cord injuries. Methods for managing these problems are active areas of medical research. An important approach is the use of electrical stimulation or neural prosthetics. A particular direction in the application of electrical stimulation is the use of a small, fully implanted microstimulator that is activated with radio frequency (RF) energy.

Conventional approaches employ various techniques for controlling the amplitude and duration of the applied electrical stimulation. Such techniques suffer from problems associated with the inefficient coupling of the input power to the device. As a result, systems have been developed which are designed to provide a selective level of power output. Such systems are often inefficient and expensive to implement. In addition, such systems do not provide for versatile controls. For example, in some systems the signal level may only be varied in accordance with the duration of the applied input signal. Other systems may allow for variable signal strength and duration but require adjustments be effected by electromechanical coupling, i.e., by the application of external magnetic fields.

Also, conventional devices have limited capability to deliver relatively high currents over prolonged application cycles. Such systems may not be satisfactory for use in connection with bowel stimulation, which may require application of relatively high currents during a treatment period for as long as 30 minutes.

SUMMARY OF THE INVENTION

The present invention is based upon the discovery that an implantable device having a selectable relatively high current output is powered and controlled by an encoded input signal having an energy component and a control component.

In a particular embodiment, the invention comprises an implantable electrical stimulator including a power storage circuit responsive to the power component of an RF input signal for storing energy to a predetermined level; and a pulse generating circuit coupled to the power storage circuit for receiving stored energy therefrom and being operative to produce stimulation pulses at a selectable output level and rate. A control circuit is coupled between the power storage circuit and the pulse generating circuit and is responsive to the energy stored in the power storage circuit for controlling the output level and pulse rate of the stimulator pulses.

In the exemplary embodiment, the power component has a relatively slow temporal characteristic, and the energy storage circuit is responsive to said relatively slow temporal characteristic whereas the pulse generating circuit is non-responsive thereto.

In the exemplary embodiment, the control component has a relatively fast temporal response and the pulse generating circuit is triggerably responsive to the relatively fast temporal characteristic for producing output pulses.

In accordance with another feature of the invention, the power component and control component of the RF signal are selectively temporally separated so that in one phase, the strength of the input pulse is determined and thereafter the pulse is triggered.

BRIEF DESCRIPTION OF THE DRAWINGS

FIG. 1 is a schematic illustration of a microstimulator in accordance with the present invention sutured or attached to the external wall of an organ.

FIG. 2 is a schematic block diagram of the implantable portion of the microstimulator according to the present invention.

FIG. 3 is a schematic block diagram illustrating the transmitter for delivering an encoded power and control signal to the microstimulator circuit illustrated in FIG. 2.

FIG. 3A is an illustration of the input signal.

DETAILED DESCRIPTION OF THE INVENTION

Figure 4:
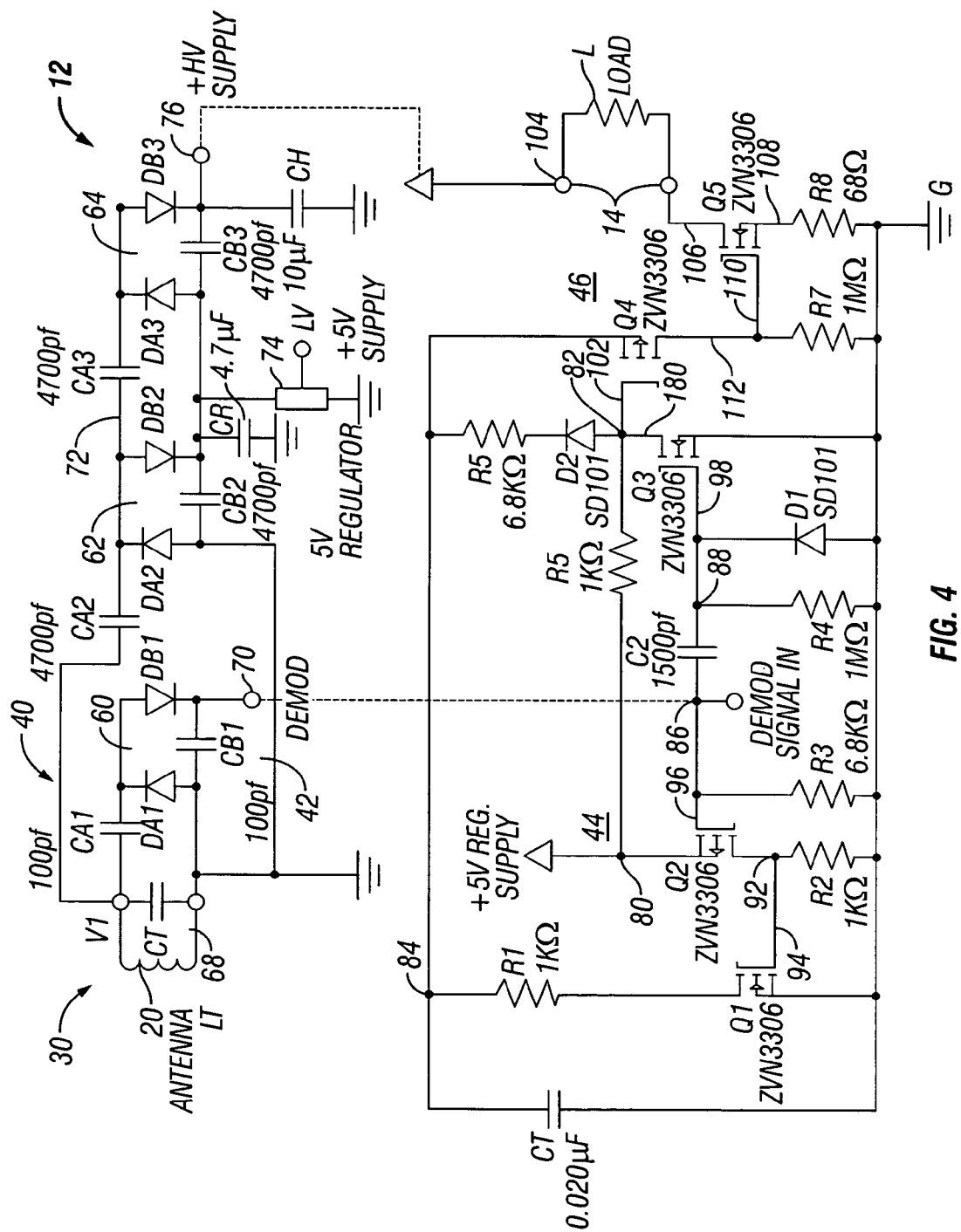
FIG. 4 is a schematic illustration of the circuit of FIG. 2.

FIG. 1 illustrates a microstimulator 10 in accordance with the present invention, which comprises an encapsulated device 12 having external electrodes 14 which may be sutured or attached to an excitable organ or muscle, such as the bowel 16 of a patient, as shown in the drawing. The microstimulator has an internal antenna (FIG. 2) for receiving an input radio frequency (RF) input signal 30. A transmitter 26, shown in FIG. 3, having a transmitter antenna 28, produces the RF signal 30 which powers and controls the microstimulator 10. According to the invention, when treatment is necessary, the transmitter antenna 28 is located proximate to the patient and the implanted microstimulator 10 which is located near the internal organ 16 is powered and controlled wirelessly by the transmitter 26.

FIG. 2 illustrates the microstimulator 10 in schematic form. The antenna receiver 20 receives the RF signal 30 and couples the signal to a power supply 40 which produces a high voltage (HV) and a low voltage (LV) outputs. A demodulator circuit 42 coupled to the power supply 40 produces a demodulator control signal (DM) which is employed for controlling the operation of the device 10. Power supply 40 delivers LV power to a charging circuit 44 which stores energy necessary for controlling the energization of the electrodes 14. The charging circuit 44 is coupled to a pulse generating circuit 46 which produces output pulses 48 on output electrodes 14 for energizing the organ represented by load resistor L. The pulses have a selectable current amplitude, pulse rate and a duration. The charging circuit 44 is responsibly coupled to the demodulator signal DM and receives the low voltage input LV as well. The pulse generating circuit 46 is likewise responsively coupled to the demodulator output and has a high voltage input as shown.

FIG. 3 illustrates the exemplary transmitter 26 in the form of RF generator 50 and wave form modulator 52. The transmitter 26 may include a variable delay control 54 and a variable time control 56 discussed hereinafter.

The transmitter 26 produces the output 30 which is a modularized RF signal 57 produced by the signal generator 50, modulated by wave form 58 produced by the wave form generator 52 as shown.

FIG. 4 schematically illustrates the circuit of the device 12. It should be understood that one or more of the various functions illustrated by the blocks in FIG. 2 may be performed by the elements described below.

Power supply 40 and the demodulator 42 are illustrated in the upper portion of FIG. 4. The power supply comprises voltage doubler circuits 60, 62 and 64. Voltage doubler 60 includes capacitors CA1 and CB1 paired with respective diodes DA1 and DB1. Voltage doubler 62 includes capacitors CA2 and CB2 paired with diodes DA2 and DB2. Voltage doubler 64 includes capacitors CA3 and CB3 paired with diodes DA3 and DB3. The diodes in each of the voltage doubler circuits are coupled in antiparallel configuration as shown. Voltage doubler 60 is coupled to a tank circuit 68 which includes an inductor LT and a parallel capacitor CT. The inductor LT represents the antenna 20. The tank circuit 68 is responsive to the modulated signal 30 produced by the transmitter 26 for producing a voltage input V1 to the input of voltage doubler 60. The input voltage V1 is doubled at the demodulator output 70 and has a wave shape 58 as illustrated in FIG. 3A, and as further detailed in FIG. 5. The wave form 58 operates to control the timing of various functions as hereinafter discussed.

Voltage doubler 62 receives input V1 which is likewise doubled at output 72. This voltage is coupled to a regulator 74 which in combination with a capacitor CR produces regulated low voltage LV.

Voltage doubler 64 receives the output of voltage doubler 62 and produces doubled voltage at high voltage output node 76 which is coupled to ground through capacitor CH.

The voltage doubler circuits 60, 62 and 64 and the tank circuit 68 have component values which establish certain voltage levels as illustrated. The selected component values noted on the drawing are exemplary of an embodiment of the invention which has operated satisfactorily.

The lower portion of FIG. 4 illustrates the charging circuit 44 and the pulse generating circuit 46. The regulator output LV is coupled to a node 80 on one side of resistor R5. The other side of the resistor R5 is coupled to the cathode of a diode D2 at node 82. The diode D2 is series connected to resistor R6 which in turn is series connected to charging capacitor at node 84. The other side of the capacitor C1 is connected to ground G as illustrated.

The demodulator output DM, noted above, is coupled to one side of a charging capacitor C2 at node 86. The other side of the charging capacitor C2 is series connected to the relatively high resistance charging resistor R4 at node 88.

The circuit of FIG. 4 includes a number of control switches including a switch Q1 which is coupled between node 84 and ground G through a relatively low resistance discharge resistor R1.

Switch Q2 is coupled between node 80 and ground G through a relatively low resistance resistor R2. The output 92 of Q2 is coupled to gate 94 of switch Q1, as shown. The demodulator input node 86 is coupled to ground G through the relatively low resistance discharge resistor R3, which is coupled to the gate 96 of switch Q2 at node 86. Diode D1 is coupled between node 88 and is forward biased relative to the ground G.

A switch Q3 is coupled between node 82 and ground as illustrated. The switch Q3 has a gate 98 coupled to the anode of diode D1 and an output 100 coupled to node 82 as illustrated.

Switch Q4 is coupled between the node 84 and ground G through a relatively high resistance resistor R7. The gate 102 of switch Q4 is coupled to node 82.

The high voltage output HV is coupled to the high voltage node 104 which represents one of the output electrodes 14, and which is coupled to the organ represented by the load resistor L. The other electrode 14 is coupled to one side 106 of a switch Q5 and to ground G through output 108 and relatively low resistance series resistor R8. Gate 110 of switch Q5 is coupled to output 112 of Q4. When the switch Q5 is on, the high voltage signal HV is applied to the load L or organ to thereby stimulate the organ function.

Figure 5:
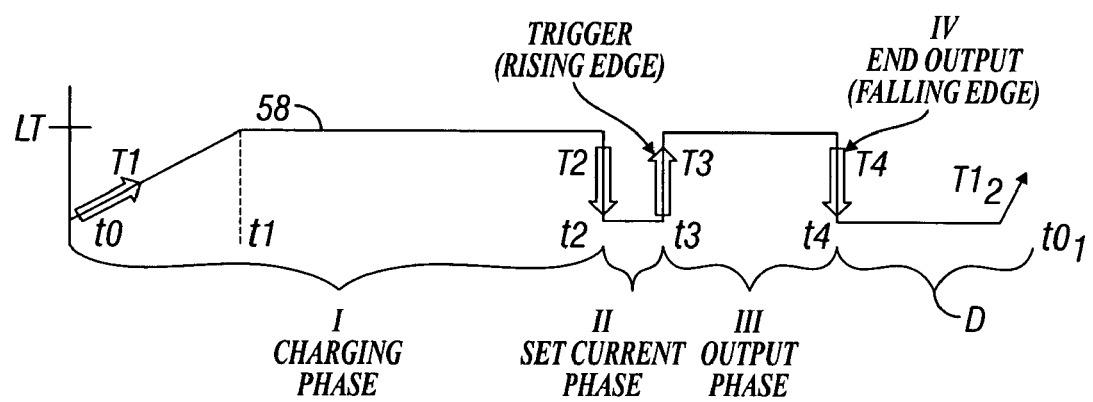
FIG. 5 is a time chart illustrating the encoding technique according to the present invention.

FIG. 5 illustrates the wave shape 58 of the output signal 30 which controls the various phases and operation and the invention. The area under the curve represents the power delivered to the device 10 during the various phases of operation. According to the invention the circuit of FIG. 4 has a Charging Phase I, Set Current Phase II, an Output Phase III and an End Output Phase IV. The various phases of operation occur during the corresponding portions of the control wave shape 58 illustrated in FIG. 5. In addition, certain transitions T1–T4 in the wave shape 58 of FIG. 5 results in corresponding responses in the circuit 12. For example, down going transition T2 on the leading edge of Phase I ends an initial Charging Phase I at time $t_2$. The rising edge T3 of the Output Phase III initiates a discharge of energy through the load L; and transition T4 at the leading edge of the End Output Phase IV at $t_4$ terminates the discharge.

Referring once again to the lower portion of FIG. 4 and the wave shape 58 in FIG. 5, the charging Phase I is described below. The wave shape 58 is received in the demodulator as noted above. The control portion of the wave shape 58 ramps up at T1 during time $t_0$–$t_1$ as indicated, and charges capacitor C1 from the low voltage supply through R5, D2 and R6. The charging rate of capacitor C1 is relatively fast and depends upon the combined resistance and capacitance of the R5, R6 and D1 of the charging circuit. At the same time capacitor C2 charges from the demodulated input through R4 as illustrated. The charging rate is relatively slow, again as a result of a combined resistance and capacitance of the elements R4 and C2 of the circuit.

During the Charging Phase I, the switchs Q1–Q5 are all off or open circuit. The charging time of C1, set by charge time control 56 (FIG. 3) is sufficient to permit the capacitor C1 to become charged to a level sufficient to operate the system. This charging level during Phase I is illustrated by the level LI on wave shape 58 when capacitors C1 and C2 are fully charged. During Phase I the switches Q1–Q5 are off. At time $t_2$ the wave shape 58 transitions down at transition T2 initiating Set Current Phase II. The gate 96 on switch Q2 goes low through resistor R2 to the node 86 causing switch Q2 to turn on, which in turn causes switch Q1 to turn on as well. At this time capacitor C1 discharges through resistor R1 and switch Q1; and capacitor C2 discharges through diode D1 and resistor R3. At this time the switches Q3, Q4 and Q5 remain off. Capacitor C1 continues to receive a slow charge from the regulated supply through R5, D2 and R6.

During Phase II the capacitor C1 discharges to some voltage Vx, as determined by the time constant of C1 and R1 less the recharge supplied by the low voltage source. The length of Set Current Phase II is determined by Vx. This in turn may be established by the set current delay control 54 in the transmitter 26 (FIG. 3).

At time $t_3$ the Set Current Phase II ends by wave form transition T3. Switchs Q3–Q5 remain on during Phase III.

At transition T3 occurring at time $t_3$, the wave shape 58 steps up to initiate Output Phase III. At this time capacitor C2 recharges through the resistor R4. The rising signal at node 86 drives the gate 96 of switch Q2 high causing it to shut off which in turn shuts off switch Q1. At the same time, node 88 is driven high by the discharge of C2 through R4, causing the gate 98 on switch Q3 to go high, thereby turning switch Q3 on. As switch Q3 conducts its output at node 82 goes low thereby driving the gate 102 of switch Q4 low turning it on and thereby establishing a discharge path for capacitor C1 through Q4 and resistor R7. The discharge of C1 is relatively slow due to the high resistors of R7. The voltage drop across R7 varies as Vy. As C1 discharges, node 83 feeding the gate 10 of switch Q5 goes high thereby closing the output circuit allowing the high voltage HV supply to stimulate the muscle, represented by the load resistor L, through switch Q5 and resistor R8. The discharge for output Output Phase III terminates at time $t_4$ upon the occurrence of transition T4, the End Output Phase IV begins.

The duration of the Output Phase III depends on the voltage level at gate 110 of switch Q5, which in turn, is a function of the charge level on capacitor C1. As the voltage on R7 drops below Vy the switch Q5 turns off. When the wave shape 58 goes low at time $t_4$, Q3, Q4 and Q5 turn off, and in a fashion similar to the occurrence at time $t_2$, switch Q1 and Q2 turn on discharging capacitor C1 through resistor R1, and discharging capacitor C2 through diode D1 and R3. After some fixed dead time D, during End Output Phase IV, the cycle may be restarted at time $t_0$. In this connection it is possible to eliminate the charging period $t_0$–$t_1$ as the capacitor C1 retains some residual charge and may be brought up to its selected operating level LI relatively quickly thereafter.

The system according to the invention has the capability to provide electrical stimulation for muscles and organs requiring pulses with relatively large currents, for example, around 10–100 ma; a relatively long duration, for example, 1,000 microseconds per pulse. The fully implantable microstimulator of the invention uses RF signals for both power and control. Since the energy and control is externally provided, batteries and complex control circuitry are not needed for the implant. The use of RF energy eliminates the need for wires or cables that would be prone to breakage and requite an exit site through the skin of the patient that would be a route for infection.

The system uses a signaling method, which allows varying the parameters of stimulation so that the current amplitude, pulse width and pulse repetition rate can be controlled externally as needed. A prototype device has been produced which has an output exceeding 50 miliamps, 1,000 microseconds and 40 pulses per second. However, depending on the operation, the parameters may be charged by varying the value of the various components. The design for the implant allows varying these parameters on a pulse-by-pulse basis so that with a sophisticated external transmitter, complex results such as ramping and current or pulse with up and down are possible.

The exemplary device was devised for using aiding bowel movements. However, other possible uses are available such as for aiding in bladder control and respiratory cough assistance.

What is claimed is:

1. An implantable electrical stimulator for neural prosthesis powered by and operative in response to an externally applied radio frequency (RF) signal having a power component and a control component for producing stimulation pulses operative to stimulate function of muscles and organs in a patient comprising:
   a power storage circuit including a passive energy storage device responsive to the power component of the RF signal for storing energy without batteries to a selected level at least sufficient to power the electrical stimulator for an impending stimulation cycle;
   a pulse generating circuit coupled to the power storage circuit for receiving stored energy therefrom and being operative to produce the stimulation pulses at a selectable output level and predetermined rate and;
   a control circuit coupled between the power storage circuit of the pulse generating circuit being responsive to the energy level stored in the storage circuit for controlling the output level of the stimulator pulses.

2. The implantable electrical stimulator according to claim 1 wherein the power component has a relatively slow temporal characteristic and the energy storage circuit is responsive to said relatively slow temporal characteristic to store energy over a selected interval.

3. The implantable electrical stimulator of claim 1, wherein the control component has a relatively fast temporal characteristic and the pulse generating circuit is triggerably responsive to said relatively fast temporal characteristic for producing output pulses.

4. The implantable electrical stimulator of claim 1, wherein the power component and the control component of the RF signal are selectively temporally separated for selectively controlling the level of energy stored in the energy storage circuit.

5. The implantable electrical stimulator of claim 1, wherein the control circuit produces an output of greater than 10 miliamps.

6. The implantable electrical stimulator of claim 5, wherein the control circuit produces an output current of 15 milamps.

7. The implantable electrical stimulator of claim 1, wherein the control circuit produces output pulses of about 1,000 microseconds.

8. The implantable electrical stimulator of claim 1, wherein the control circuit produces 40 pulses per second.

9. The implantable electrical stimulator of claim 1, being operable for a duration sufficient to stimulate the organ to function.

10. The implantable electrical stimulator of claim 1, including an external transmitter for producing the RF signal.

11. The implantable electrical stimulator of claim 1, wherein the RF generator is operative for producing at least one of a selective charge time and a selected delay time in the RF signal for varying the amplitude and duration of the output signal respectively.

12. A method for operating an implantable electrical stimulator for neural prosthesis comprising the steps of:
   providing an externally applied radio frequency (RF) signal having a power component and a control component;
   storing energy employing a passive energy storage device without to a selected level at least sufficient to power the electrical stimulator;
   receiving stored energy to produce the stimulation pulses at a selectable rate; and
   controlling the output level of the stimulator pulses in accordance with the stored energy level.

13. An implantable electrical stimulator for neural prosthesis powered by and operative in response to an externally applied radio frequency (RF) signal having a power component and a control component for producing stimulation pulses operative to stimulate function of muscles and organs in a patient comprising:
   a power storage circuit including a passive energy storage responsive to the power component of the RF signal for storing energy without batteries to a selected level at least sufficient to power the electrical stimulator;

a pulse generating current coupled to the power storage circuit for receiving stored energy therefrom and being operative to produce the stimulation pulses at a selected output level and rate; and a control circuit coupled between the power storage circuit of the pulse generating circuit being responsive to the energy level stored in the storage circuit for controlling the output level of the stimulator pulses; and; wherein the power component and the control component of the RF signal are selectively temporally separated for selectively controlling the level of energy stored in the energy storage circuit.

14. The implantable electrical stimulator according to claim 1, wherein the power component is temporarily stored in the storage circuit.

* * * * *